United States Patent [19]
Anbar

[11] Patent Number: 6,035,225
[45] Date of Patent: Mar. 7, 2000

[54] DETECTION OF CANCEROUS LESIONS BY MEASURING NITRIC OXIDE CONCENTRATIONS IN TISSUE

[75] Inventor: Michael Anbar, Williamsville, N.Y.

[73] Assignee: Omnicorder Technologies, Stoneybrook, N.Y.

[21] Appl. No.: 09/076,532

[22] Filed: May 12, 1998

Related U.S. Application Data

[63] Continuation-in-part of application No. 08/368,161, Jan. 3, 1995, Pat. No. 5,810,010.

[51] Int. Cl.[7] ........................................................ A61B 5/05
[52] U.S. Cl. .......................... 600/407; 600/322; 600/340
[58] Field of Search ...................... 600/407, 411, 600/309, 310, 322, 323, 324, 326, 334, 340

[56] References Cited

U.S. PATENT DOCUMENTS

| | | | |
|---|---|---|---|
| 4,809,701 | 3/1989 | Le Bihan et al. | 128/653 |
| 5,205,293 | 4/1993 | Ito et al. | 128/691 |
| 5,207,222 | 5/1993 | Koizumi et al. | 128/653 |
| 5,207,227 | 5/1993 | Powers | 128/691 |
| 5,233,994 | 8/1993 | Shmulewitz | 128/661 |
| 5,336,388 | 8/1994 | Leader et al. | 204/406 |
| 5,358,703 | 10/1994 | Lai | 424/9 |
| 5,445,157 | 8/1995 | Adachi et al. | 128/664 |
| 5,588,437 | 12/1996 | Byrne et al. | 128/691 |
| 5,603,820 | 2/1997 | Malinski et al. | 205/781 |
| 5,810,010 | 9/1998 | Anbar | 600/473 |

OTHER PUBLICATIONS

Cancer Letters 84 (1994) Michael Anbar—Hyperthermia of the cancerous breast: analysis of mechanism; pp. 23–29.

Journal of Pain and Sympton Management; Special Article—Role of Nitric Oxide in the Physiopathology of Pain; Michael Anbar and Barton M. Gratt; pp. 225–254; Oct. 1997.

Fast Dynamic Area Telethermometry (DAT) of the Human Forearm With A Ga/As Quantum Well Infrared Focal Plane Array Camera; Michael Anbar, M. W. Grenn, M. T. Marino, L. Milescu and K. Zamani; pp. 105–118.

Manifestation of Neurological Abnormalities Through Frequency of Skin Temperature Regulation; Michael Anbar, James C. Montoro, Kyu Ha Lee and Sean D'Arcy; 1991; pp. 234–241.

Biomedical Thermology; 13; Local "Micro" Variance In Temperature Distribution Evaluated By Digital Thermography; Michael Anbar and Robert F. Haverley; pp. 173–187, 1994.

Simultaneous Acquisition of Thermal and Visible Images in A Scanning Infrared Camera; Shahram Hejazi, Omid A. Moghadam, Robert A. Spangler and Michael Anbar; SPIE vol. 2020 Infrard Technology XIX, pp. 510–516. 1993.

*Primary Examiner*—Brian L. Casler
*Attorney, Agent, or Firm*—Hodgson, Russ, Andrews, Woods & Goodyear LLP

[57] ABSTRACT

The present invention involves the measurement of nitric oxide in interstitial fluid extracted by a thin needle from a body tissue, and particularly a human breast. The diffuse nature of nitric oxide means that the sample of body fluid does not need to be taken directly from the lesion to indicate that cancerous cells are present in the vicinity. Therefore, the presence of nitric oxide in the extracted body fluid is a direct indicator of the presence of a cancerous lesion in the vicinity.

20 Claims, No Drawings

DETECTION OF CANCEROUS LESIONS BY MEASURING NITRIC OXIDE CONCENTRATIONS IN TISSUE

CROSS-REFERENCE TO RELATED APPLICATION

The present application is a continuation-in-part of application Ser. No. 08/368,161, filed Jan. 3, 1995, now U.S. Pat. No. 5,810,010.

BACKGROUND OF THE INVENTION

1. Field of Invention

The present invention relates generally to cancer detection and, more particularly, to cancer detection involving the measurement of nitric oxide associated with cancerous tissue. The present invention directly detects nitric oxide in tissue and, therefore, by its presence serves as an indicator of cancerous cells. While nitric oxide dependent cancer detection is applicable throughout the human body, it is particularly applicable to the human breasts. Nitric oxide concentration is determined by drawing a sample of interstitial fluid from a breast, preferably through a small gauge needle, and analyzing the fluid using conventional techniques.

Before the present invention, a full work-up, generally comprising an ultrasonic scan, needle or incision biopsy, or stereotactic biopsy is preceded by a positive finding on a breast cancer screening test, such as a positive mammographic image, and followed by a histopathological study. The present invention is not necessarily a screening test but is used as a confirmation of a positive result from a screening test. If the results of the present test are confirmatory, i.e., nitric oxide is present in the breast tissue, a biopsy is performed as a double check. If, on the other hand, it is determined that nitric oxide is not present in the breast and, consequently, that the screening test was erroneous, the patient is spared the trauma of having to undergo the full work-up including the biopsy. In that respect, confirmation of cancerous lesions by measuring nitric oxide concentrations in tissue has many significant differences and advantages over conventional breast cancer tests, as well as cancer detection methods in general.

2. Prior Art

Up to now, cancerous lesions have been generally located by their space occupying properties detectable by palpation or by imaging techniques, such as X-ray mammography (XRM), X-ray computerized tomography (CT), ultrasonic imaging, or magnetic resonance imaging (MRI). In certain cases, such as in a human breast, detection of cancer is also made possible by the enhanced blood supply (hyperperfusion) associated with the neoplastic lesion. A technique which takes advantage of this hyperperfusion is Dynamic Area Telethermometry (DAT), which is fully described in the Applicant's patent application Ser. No. 08/368,161 filed Jan. 3, 1995. That application is licensed to the assignee of the present invention and incorporated herein by reference.

The various prior art cancer detection methods are based on secondary indicators resulting from the growth of the cancerous lesions. For example, XRM uses the higher density of calcium minerals and the higher absorbance of X-rays in calcium atoms, due to the photoelectric effect, to detect microcrystals of calcium minerals, generally calcium phosphates, that deposit interstitially in cancerous tissue. The characteristic shadow of the relatively opaque microcrystals of calcium minerals on the radiograms indicates their presence in tissue. Since pathological microcalcification occurs subsequent to tumor formation, it occurs later than the proliferation of cancerous cells producing nitric oxide, and the immune response to neoplastic cells, which invokes macrophage activity that also produces nitric oxide. Therefore, nitric oxide is present in a cancerous breast before detection is possible by XRM. Also, one of the major draw-backs of XRM as a breast cancer screening test is the occurrence of microcalcification or calcification in benign lesions. Hence, only a fraction of breasts that manifest microcalcification contain malignant tissue. False positive XRM results are common, and lead to full diagnostic work-ups which often prove to be negative for breast cancer.

In order to prevent full diagnostic work-ups predicated on false positive XRM results, there is needed a confirmation test that is easy to administer, inflicts a minimal amount of trauma to the patient and gives accurate results on which a physician can confidently subject the patient to a surgical procedure to remove the lesion, if present. Since the outcome of treatment of cancer, and particularly breast cancer, is more favorable the earlier and more accurately the cancer is detected, the present invention is a substantial advancement in improving public health by conclusively indicating the presence of cancerous lesions.

SUMMARY OF THE INVENTION

NO diffuses throughout in the interstitial space proximate a cancerous lesion. This has been discussed extensively by Dr. Anbar in the Journal of Pain and Symptom Management 14:225–254, 1997. Augmented immune response, such as encountered in local infections, autoimmune diseases and cancer, is associated with enhanced NO production. Under certain conditions, such as in breast cancer, autocatalytic production of NO may occur, enhancing the local level of NO. The latter process has been extensively discussed by Dr. Anbar in Cancer Letters 84:23–29, 1994. Therefore, extracting a sample of interstitial fluid from a tissue of interest, such as a human breast, and testing that fluid for the presence of NO is determinative of the presence, or lack thereof, of cancerous lesions according to the present invention.

DETAILED DESCRIPTION OF THE PREFERRED EMBODIMENTS

Healthy tissue, such as a healthy human breast, is devoid of interstitial nitric oxide. Conversely, cancerous cells are known to produce nitric oxide. The interstitial concentration of nitric oxide is further augmented by the immune response to neoplastic cells which invokes macrophage activity that also produces nitric oxide. It is known that breast cancer cell and macrophage generated NO diffuses throughout the surrounding tissue and interacts with the vasoconstrictive receptors in the arterioles and venules to vasodilate the vasculature. Vasodilation results in enhanced perfusion of the capillary bed associated with the spread of NO. As a consequence of the characteristic multiphasic synergistic action of NO, discussed in Dr. Anbar's previously referenced paper in the Journal of Pain and Symptom Management 14:225–254, 1997 and in previous publications cited there, vasodilation augmented perfusion enhances the growth of breast cancer cells. The rate of production of NO is further enhanced by the presence of ferritin, the level of which is significantly elevated in cancerous breast tissue. $Fe^{2+}$ released from ferritin consequently produces more NO synthase (NOS), an iron carrying enzyme which produces NO from arginine, and thus results in a further increase in the rate of production of NO.

Furthermore, NO has been shown to release $Fe^{2+}$ from ferritin by forming an NO-ferritin complex which consequently results in an autocatalytic production of NO. $Fe^{2+}$ reacts with nitrite, the oxidation product of NO, to reform NO, and it also eliminates superoxide radicals ($HO_2$) which are normally the major scavengers of NO. Elimination of $HO_2$ maintains the local high level of NO, and hyperperfusion of the tissues surrounding the cancerous lesion. The ferritin dependent enhancement of NO production seems to be specific to neoplastic cells and is less likely to occur in other inflammatory situations, including those induced by microorganisms. All of these autocatalytic effects overshadow the negative feedback of the NO level on the rate of enzymatic NO production.

One of the major drawbacks of a needle biopsy according to the conventional breast cancer tests is a false negative. If the needle does not directly contact or extract cancerous tissue, the biopsy results may indicate the absence of cancer when, in fact, a cancerous lesion is present. In contrast, the volume of tissue that is permeated with nitric oxide-containing interstitial fluid is many-fold larger than that of the tumor and its immediate surroundings. The relatively non-invasive nature of drawing interstitial fluid according to the present invention means that a series of fluid samples can be extracted from the breast. Where the nitric oxide concentration is highest, the existence of a cancerous lesion is most likely. The locus of the lesion is then followed by a conventional biopsy to reconfirm malignancy, followed by excision of the tumor.

Therefore, detection certainty according to the present invention is predicated on the broad perfusion of NO generated by the cancerous cells and by macrophages. A needle aspiration is all that is required to extract a sample of interstitial body fluid from the breast. However, the clinician need not directly contact the cancerous lesion with the needle. Unlike the conventional needle biopsy which requires a large diameter needle under local anesthetic, i.e., a needle of about 1 mm. in diameter, to pick up cancerous cells, the needle used in the present invention is quite thin, for example 18 gauge, minimizing traumatic puncture and avoiding the use of local anesthetics. The extracted fluid is then analyzed for the presence of nitric oxide which, if present, is directly indicative of the presence of cancer. In other words, the presence of nitric oxide in the extracted interstitial fluid sample is a conclusive indicator of a cancerous lesion in the vicinity.

Preferred methods of measuring the concentration of NO in the extracted interstitial fluid include chemiluminescence, electrochemical analysis and electron paramagnetic resonance (EPR). These and other methods of detecting nitric oxide are fully described in Methods in Nitric Oxide Research, edited by Martin Feelisch and Jonathan S. Stanler (1996), which is incorporated herein by reference.

According to a further embodiment of the present invention, interstitial fluid is continuously aspirated from a surgical site and run through a nitric oxide detector. This provides the physician with a real-time indication of the nitric oxide concentration and, therefore, presence or lack thereof of cancerous tissue remaining at the surgical site. Once the nitric oxide detector reading is zero, the physician can be confident that all of the cancerous lesion has been removed. The conventional alternative is surgical excision until there is no remaining visual indication of the cancerous lesion. However, this is not as conclusive as taking a nitric oxide reading of the extracted interstitial fluid as it is possible to overlook cancerous growth, or in the alternative, cut out far too much tissue than is actually needed in an attempt to be thorough.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A method for detecting cancerous tissue, comprising the steps of:
    a) extracting a plurality of samples of body fluid from various locations in a body tissue;
    b) measuring a concentration of nitric oxide in the plurality of body fluid samples; and
    c) determining at least one of a location of a cancerous lesion in the body tissue by the presence of nitric oxide in at least one of the body fluid samples and determining the absence of a cancerous lesion in the body tissue by the absence of nitric oxide in the body fluid samples.

2. The method of claim 1 including extracting the body fluid from cancerous tissue.

3. The method of claim 1 including extracting the body fluid from non-cancerous tissue.

4. The method of claim 1 including extracting the body fluid from non-cancerous tissue proximate to cancerous tissue.

5. The method of claim 1 wherein measuring includes subjecting the body fluid samples to one of the group consisting of a chemiluminescence analysis, a electrochemical analysis and an EPR analysis.

6. The method of claim 1 wherein the tissue is a human breast.

7. The method of claim 1 including acquiring the body fluid samples using a needle.

8. The method of claim 7, wherein the needle is of an 18 gauge size.

9. The method of claim 1 wherein the tissue from which the body fluid samples are extracted in unanesthetized.

10. The method of claim 1 wherein the body fluid samples are devoid of nitric oxide and determining the tissue to be healthy.

11. A method for detecting cancerous tissue in a human breast, comprising the steps of:
    a) providing a needle;
    b) inserting the needle into the human breast to aspirate a plurality of samples of body fluid from various locations in the breast;
    c) measuring a concentration of nitric oxide in each of the body fluid samples; and
    d) utilizing the measurements to determine a location of a cancerous lesion in the breast or, in the alternative, determining the absence of a cancerous lesion in the breast by the absence of nitric oxide in the body fluid samples.

12. The method of claim 11, including aspirating the body fluid samples from cancerous tissue.

13. The method of claim 11, including aspirating the body fluid samples from non-cancerous tissue.

14. The method of claim 11, including aspirating the body fluid samples from non-cancerous tissue proximate to cancerous tissue in the breast.

15. The method of claim 11, wherein the tissue from which the body fluid is aspirated is unanesthetized.

16. The method of claim 11, wherein the body fluid samples are devoid of nitric oxide and determining the human breast to be healthy.

17. The method of claim 11, wherein measuring includes subjecting the body fluid samples to one of the group consisting of a chemiluminescence analysis, a electrochemical analysis and an EPR analysis.

18. A method for performing a surgical procedure to remove a cancerous lesion from a tissue, comprising the steps of:
   a) surgically excising the tissue from a surgical site containing the cancerous lesion;
   b) aspirating body fluid from the surgical site as the cancerous lesion is being excised;
   c) measuring a concentration of nitric oxide in the aspirated body fluid;
   d) discontinuing excision of the tissue from the surgical site once the measurement of nitric oxide in the aspirated body fluid indicates that the body fluid is devoid of nitric oxide and, consequently, the cancerous lesion has been removed; and
   e) surgically repairing the site of the removed cancerous lesion.

19. A method for detecting cancerous tissue, comprising the steps of:
   a) extracting at least one sample of body fluid from a body tissue;
   b) measuring a concentration of nitric oxide in the body fluid by subjecting the body fluid to one of the group consisting of a chemiluminescence analysis, a electrochemical analysis and an EPR analysis; and
   c) determining at least one location of a cancerous lesion in the body tissue by the presence of nitric oxide in the at least one body fluid sample and determining the absence of a cancerous lesion in the body tissue by the absence of nitric oxide in the at least body fluid sample.

20. A method for determining whether tissue is healthy or cancerous tissue, comprising the steps of:
   a) extracting a sample of body fluid from a body tissue;
   b) measuring a concentration of nitric oxide in the body fluid sample; and
   c) determining the body fluid sample to be devoid of nitric oxide and, consequently, healthy.

* * * * *